(12) United States Patent
Goettel et al.

(10) Patent No.: US 6,361,571 B1
(45) Date of Patent: Mar. 26, 2002

(54) AGENTS AND METHOD FOR PRODUCING SEMI-PERMANENT COLORATIONS OF KERATIN FIBERS

(75) Inventors: Otto Goettel, Marly; Aline Pirrello, Givisiez, both of (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/462,315
(22) PCT Filed: Feb. 26, 1999
(86) PCT No.: PCT/EP99/01266
  § 371 Date: Jan. 4, 2000
  § 102(e) Date: Jan. 4, 2000
(87) PCT Pub. No.: WO99/59529
  PCT Pub. Date: Nov. 25, 1999

(30) Foreign Application Priority Data

May 16, 1998 (DE) .......................... 198 22 198

(51) Int. Cl.$^7$ ................................. A61K 7/13
(52) U.S. Cl. .................. 8/405; 8/407; 8/423; 8/568; 8/571; 8/573; 8/638; 8/639; 8/643; 8/644
(58) Field of Search ............................. 8/405, 407, 423, 8/568, 571, 573, 638, 639, 643, 644

(56) References Cited

U.S. PATENT DOCUMENTS

| | | | | |
|---|---|---|---|---|
| 3,681,345 A | * | 8/1972 | Bland | 544/300 |
| 4,218,432 A | * | 8/1980 | Watanabe et al. | 548/366.1 |
| 4,266,014 A | * | 5/1981 | Moelants et al. | 548/366.1 |
| 4,288,534 A | * | 9/1981 | Lemahieu et al. | 548/36.1 |
| 4,440,852 A | * | 4/1984 | Onishi et al. | 548/366.1 |
| 5,013,636 A | * | 5/1991 | Ohno et al. | 430/522 |
| 5,352,247 A | * | 10/1994 | Adam | 8/676 |
| 5,371,201 A | * | 12/1994 | Hurter | 534/819 |

OTHER PUBLICATIONS

Houben–Weyl 5/1 D (4–th Edition, 1954), pp. 231, 296 and 227.
"Chemie In Unserer Zeit" (Chemistry In Our Times) 1978, No. 1, pp. 1–11.
Houben–Weyl 5/1d, 4th Edition (1954), Page 227.ff (no month available).

* cited by examiner

*Primary Examiner*—Margaret Einsmann
(74) *Attorney, Agent, or Firm*—Michael J. Striker

(57) ABSTRACT

The object of the present invention is a colorant for the semi-permanent tinting of keratin fibers, said colorant being based on a combination of nonoxidative dyes and polymethine dyes of the tautomeric formula (Ia)/(Ib)

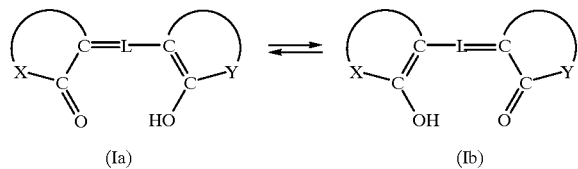

and a method for tinting keratin fibers.

10 Claims, No Drawings

AGENTS AND METHOD FOR PRODUCING SEMI-PERMANENT COLORATIONS OF KERATIN FIBERS

The present invention relates to nonoxidative colorants for keratin fibers, for example hair or wool, based on a combination of natural or synthetic nonoxidative dyes (known as "direct dyes") and polymethine dyes, as well as to a method for coloring keratin fibers.

The coloring of hair is currently subject to the most varied trends. Whereas in the past hair was colored primarily to cover gray areas, today there is an increasing demand for integrating the hair color into current fashion as an expression of personality.

Now as before, two established methods of hair coloring are available. One of these is the oxidative hair coloring which results in very durable tints. The other method consists of the possibility of coloring hair with colorants containing nonoxidative, direct dyes (often referred to as toners). Although the dyes used for this purpose are optimized for dyeing performance as well as for remaining on the hair as long as possible, the color shade gradually weakens with every hair washing. Thus, as a rule and depending on the product used and the type of hair, such colorants do not last more than a maximum of 10 hair washings.

Hence, a need exists for nonoxidative colorants which besides good coloring properties have improved color stability, particularly in terms of wash-out resistance.

Surprisingly, we have now found that colorants based on a combination of natural or synthetic nonoxidative dyes and polymethine dyes (in the following also referred to as "oxonol dyes") produce an outstanding and, in particular, very long-lasting coloring of keratin fibers.

Oxonol dyes have been known for a long time, and a wide range of substitution patterns can be found in the literature. A review of these dyes can be found, for example, in Houben-Weyl 5/1d, 4th edition (1954), page 227 ff. Some of these oxonol dyes are also available commercially.

By means of the colorants of the invention, it is possible to achieve color shades of a modified natural tone, but particularly those in the fashionable range. Moreover, besides the said color shades, it is possible to obtain a number of vivid color highlights, particularly in the bright-red to blue range. As a result of the high tinting power of the dyes and their high substantivity, the original fiber color can be covered very effectively. As a result, it is possible to satisfy the aforementioned desire to integrate the hair color into fashion and to provide an expression of personality.

The object of the present application is therefore a colorant for keratin fibers, for example furs, feathers, wool and hair, particularly human hair, characterized in that it contains a combination of (a) at least one natural or synthetic nonoxidative dye and (b) at least one polymethine dye having the tautomeric formula (Ia)(Ib) or a physiologically tolerated salt thereof

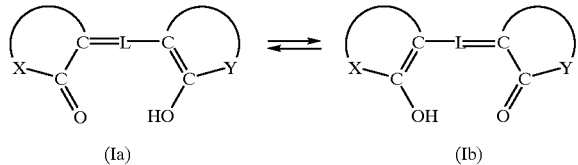

(Ia)  (Ib)

wherein in general formula (Ia)(Ib) X and Y independently of each other and together with the two carbon atoms of the ring system indicated in formula (Ia)(Ib) represent the elements needed for the formation of a five-membered or six-membered heterocyclic ring, and L stands for a linking group of general formula

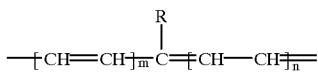

wherein R denotes a hydrogen atom, a phenyl, methyl or carboxamido group or a halogen atom, and indices m and n are equal to 0, 1 or 2, the sum of m and not exceeding 2.

For example, the five-membered or six-membered heterocyclic ring in general formula (Ia)(Ib) can be a pyrazolone, pyridone, isoxazolone, dioxothiazoline, rhodanine, dioxoimidazolidine, barbituric acid or thiobarbituric acid group, the two ring systems present in general formula (Ia)(Ib) being equal or different. Preferably, taking into account their tautomeric forms, these two ring systems are identical, and L stands for a monomethine, trimethine or pentamethine unit.

Suitable physiologically tolerated salts of the compounds of formula (Ia)(Ib) are, in particular, the alkali metal and ammonium salts, for example the ammonium, triethylammonium, sodium, potassium, N-methylmorpholinium, monoethanolammonium, diethanolammonium and triethanolammonium salts among which the sodium, potassium and particularly the ammonium salts are preferred.

Written in their acid form, the dyes of formula (I) used in the colorant of the invention contain polymethine dyes of general formulas (II) to (IV), presented in their possible tautomeric forms

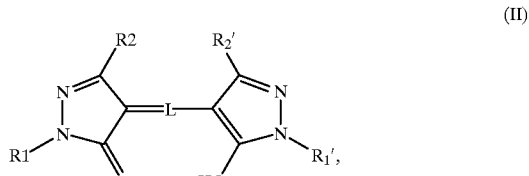
(II)

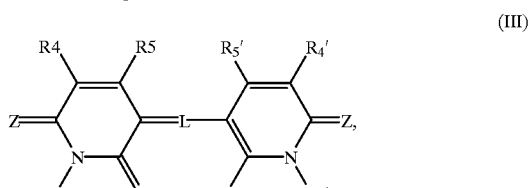
(III)

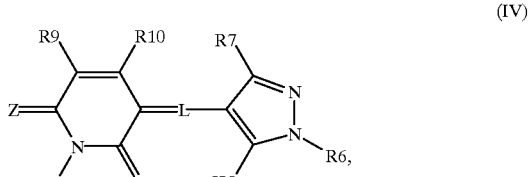
(IV)

wherein R1, R1' and R6 denote hydrogen, a straight-chain or branched C1 to C8 alkyl, hydroxyethyl, dihydroxypropyl, methoxyethyl, carboxyethyl or C1 to C4 sulfoalkyl group, a phenyl radical, a phenyl radical substituted with one or more halogen atoms, a phenyl radical substituted with one or two sulfonic acid groups, a phenyl radical substituted with one or two carboxylic acid groups, a phenyl radical substituted with one or more unbranched or branched C1 to C8 alkyl groups or C1 to C8 alkoxy groups, a benzyl radical, a benzyl radical substituted with one or more halogen atoms, a benzyl radical substituted with a C1 to C4 alkyl, a hydroxyl, methoxy, carboxyl, nitro or amino group or a five-membered or six-membered saturated or unsaturated heterocyclic ring, R1 and R1' being equal or different;

R2, R2' and R7 denote hydrogen, a branched or unbranched C1 to C6 alkyl group, a phenyl radical, an amino group which can also be acylated or sulfonylated, an acetyl or methoxy or a carboxylic acid group esterified with a straight-chain or branched C1 to C8 alcohol or ethylene glycol monomethyl ether or ethylene glycol monoethyl ether, or a carboxamido, carboxanilido or 2-amino-2-oxyethyl or nitrile group, R2 and R2' being equal or different; and R3, R3' and R8 denote hydrogen, a straight-chain or branched C1 to C11 alkyl group, a monohydroxyalkyl group, a straight-chain or branched C1 to C11 dihydroxyalkyl group, a straight-chain or branched C1 to C11 alkoxyalkyl group, a straight-chain or branched C1 to C11 monoalkylamino group, an amino group having formula $(CH_2)_x$—$NR11R12$ (wherein x stands for an integer from 0 to 3 and R11 and R12 independently of each other denote a C1 to C3 alkyl group), a C2 to C4 sulfoalkyl or carboxyalkyl group, a phenyl group or a phenyl group substituted with one or more halogen atoms, or a phenyl group substituted with one or two sulfonic acid groups, or with one or two carboxyl groups, or with one or more unbranched or branched C1 to C8 alkyl groups or with C1 to C8 alkoxy groups, or a benzyl group or a benzyl group substituted with one or more halogen atoms, or with a C1 to C4 alkyl, hydroxyl, methoxy, nitro or amino group, or a phenylethyl group, a five-membered or six-membered aromatic or nonaromatic heterocyclic ring which can be linked directly through a methylene group, a pyrolidino, morpholino, piperazino, piperidino or pyridino (C2 or C3) alkyl group or a trialkylammonium group of formula $R13$—$N(R14)_3^+$ (wherein R13 denotes a C1 to C6 alkylene group and R14 denotes a methyl or ethyl group, the total number of carbon atoms in the molecule being 5 to 9), R3 and R3' being equal or different, and R4, R4' and R9 denote hydrogen, a nitrile, carboxylate ester, carboxamido, sulfonic acid, sulfomethyl or methanesulfonyl group or a pyridinium or imidazolium radical, R4 and R4' being equal or different, and R5, R5' and R10 denote hydrogen or a C1 to C4 alkyl group or a C5–C6 cycloalkyl, phenylethyl, methoxyphenyl, benzyl, phenyl or carboxyl group, R5 and R5' being equal or different, and Z denotes oxygen or a radical of formula $C(CN)_2$, $C(CN)COOQ$ or $C(COOQ)_2$ wherein Q denotes a C1 to C8 alkyl group or an ethylene glycol mono-(C3 to C7)-alkyl ether, and L denotes a linking group of general formula

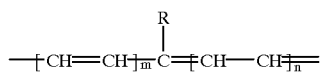

wherein R denotes a hydrogen atom, a phenyl, methyl or carboxamido group or a halogen atom, and the indices m and n equal 0, 1 or 2, the sum of m and n not exceeding 2.

Particularly preferred are dyes of general formulas (II) to (IV) and the salts thereof wherein R1 and R1' are equal and denote hydrogen, a straight-chain or branched C1 to C4 alkyl group, a hydroxyethyl, dihydroxypropyl, methoxyethyl or C2 to C4 sulfoalkyl group, a phenyl radical or a phenyl radical substituted with one or more halogen atoms, one or two sulfonic acid groups, a methyl or methoxy group, or a benzyl radical or a benzyl radical substituted with a halogen atom, a methyl, hydroxyl, methoxy, nitro or amino group, and R2 and R2' are equal and denote a methyl group or an amino group which can also be acylated, or a carboxyl group possibly esterified with a C1 to C3 alcohol, and R3 and R3' are equal or different and denote hydrogen, a straight-chain C1 to C4 alkyl group, a hydroxyethyl, methoxyethyl, methoxypropyl or sulfoethyl group or a phenyl radical or a phenyl radical substituted with a halogen atom, a sulfonic acid or methyl or methoxy group, or a benzyl radical or a benzyl radical substituted with a halogen atom, a methyl, hydroxyl, methoxy, nitro or amino group or a five-membered or six-membered aromatic or nonaromatic heterocyclic ring which can be linked directly or through a methylene group; an amino group, a C1 to C4 monoalkylamino group or a dialkylamino group with a total of 2 to 8 carbon atoms in the molecule, or a trialkylammoniumalkyl group of formula $R13$—$N(R14)_3^+$ (wherein R13 denotes a C1 to C6 alkylene group and R14 denotes a methyl or ethyl group, the total number of carbon atoms in the molecule being equal to 5 to 9), and R4 and R4' are equal and denote hydrogen, a nitrile, carboxamido, sulfonic acid, sulfomethyl, methanesulfonyl, pyridinium, or imidazolium group, and R5 and R5' are equal and denote hydrogen, a methyl or nitrile group or a substituted or unsubstituted phenyl radical, and R6 denotes hydrogen, a straight-chain or branched C1 to C4 alkyl group or a hydroxyethyl, dihydroxypropyl, methoxyethyl or C2 to C4 sulfoalkyl group or a phenyl radical or a phenyl radical substituted with one or more halogen atoms, one or two sulfonic acid groups, a methyl or methoxy group; a benzyl radical or a benzyl radical substituted with a halogen atom, or a methyl, hydroxyl, methoxy, nitro or amino group, and R7 denotes a methyl group or an amino group which can also be acylated, a carboxyl group or a carboxyl group esterified with a C1 to C3 alcohol, and R8 denotes hydrogen, a straight-chain C1 to C4 alkyl group, a hydroxyethyl, methoxyethyl or sulfoethyl group, a phenyl radical or a phenyl radical substituted with a halogen atom, sulfonic acid, methyl or methoxy group; a benzyl radical or a benzyl radical substituted with a halogen atom or a methyl, hydroxyl, methoxy, nitro or amino group; or a five-membered or six-membered aromatic or nonaromatic heterocyclic ring linked directly or through a methylene group, an amino or C1 to C4 monoalkylamino group, a dialkylamino group with a total of 2 to 8 carbon atoms in the molecule or a trialkylammoniumalkyl group $R13$—$N(R14)_3^+$ (wherein R13 denotes a C1 to C6 alkylene group and R14 denotes a methyl or ethyl group, the total number of carbon atoms in the molecule being 5 to 9), and R9 denotes hydrogen, a nitrile, carboxamido, sulfonic acid, sulfomethyl, pyridinium or imidazolium group, and R10 denotes hydrogen, a methyl or nitrile group or a substituted or unsubstituted phenyl radical, and Z denotes oxygen or a C(CN)$_2$ group, and L is a linking group of general formula

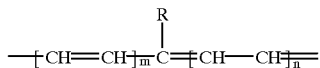

wherein R stands for a hydrogen atom or a methyl group, and the indices m and n are equal to 0, 1 or 2, the sum of m and n not exceeding 2.

The compounds shown in the following (in one of their possible tautomeric forms) are examples of the aforesaid preferred dyes of formulas (II) to (IV). Written in their acid form, they are as follows.

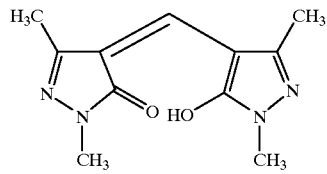

4-(5-Hydroxy-1,3-dimethyl-1H-pyrazol-4-ylmethylen)-2,5-dimethyl-2,4-dihydropyrazol-3-one (1)

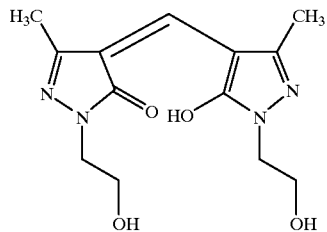

2-(2-Hydroxyethyl)4-(5-hydroxy-1-(2-hydroxyethyl)-3-methyl-1H-pyrazol-4-ylmethylen)-5-methyl-2,4-dihydropyrazol-3-one (2)

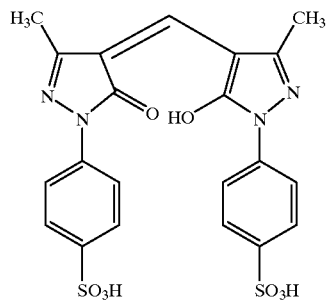

4-(5-Hydroxy-3-methyl-1-(4-sulfophenyl)-1H-pyrazol-4-ylmethylen)-5-methyl-2-(4-sulfophenyl)-2,4-dihydropyrazol-3-one (3)

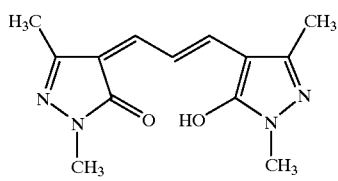

4-(3-(5-Hydroxy-1,3-dimethyl-1H-pyrazol4-yl)-allyliden)-2,5-dimethyl-2,4-dihydropyrazol-3-one (4)

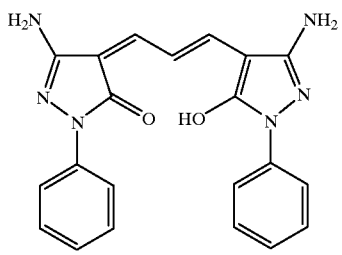

5-Amino-4-(3-(3-amino-5-hydroxy-1-phenyl-1H-pyrazol-4-yl)-allyliden)-2-phenyl-2,4-dihydropyrazol-3-one (5)

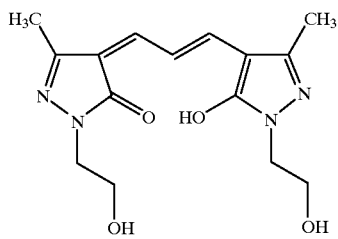

2-(2-Hydroxyethyl)-4-(3-(5-hydroxy-1-(2-hydroxyethyl)-3-methyl-1H-pyrazol-4-yl)-allyliden)-5-methyl-2,4-dihydro-pyrazol-3-one (6)

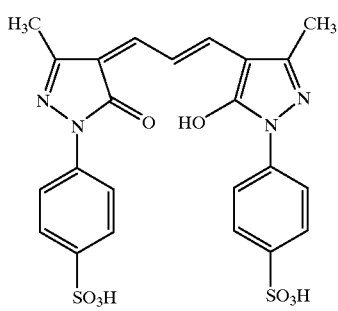

4-(3-(5-Hydroxy-3-methyl-1-(4-sulfophenyl)-1H-pyrazol-4-yl)-allyliden)-5-methyl-2-(4-sulfophenyl)-2,4-dihydro-pyrazol-3-one (7)

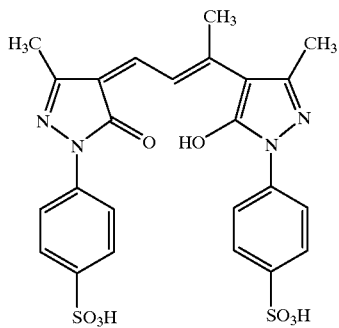

4-(3-(5-Hydroxy-3-methyl-1-(4-sulfophenyl)-1H-pyrazol-4-yl)-but-2-enyliden)-5-methyl-2-(4-sulfophenyl)-2,4-dihydropyrazol-3-one (8)

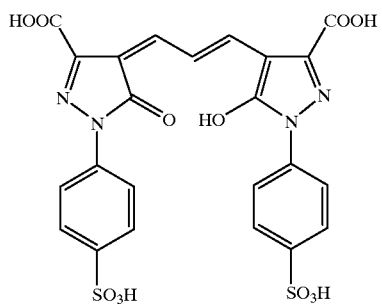

4-(3-(3-Carboxy-5-oxo-1-(4-sulfophenyl)-1,5-dihydropyrazol-4-yliden)-propenyl)-5-hydroxy-1-(4-sulfophenyl)-1H-pyrazol-3-carboxylic acid (9)

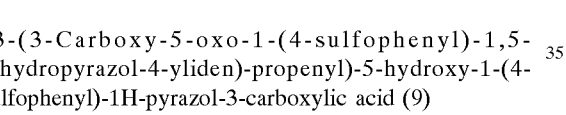

5-Hydroxy4-(3-(3-methoxycarbonyl-5-oxo-1-(4-sulfophenyl)-1,5-dihydropyrazol-4-yliden)-propenyl)-1-(4-sulfophenyl)-1H-pyrazol-3-carboxylic acid methyl ester (10)

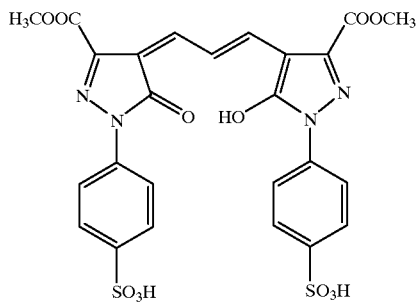

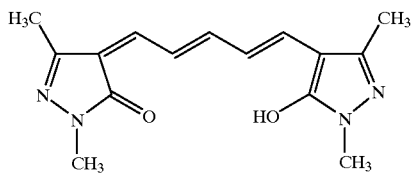

4-(5-(5-Hydroxy-1,3-dimethyl-1H-pyrazol-4-yl)-penta-2,4-dienyliden)-2,5-dimethyl-2,4-dihydropyrazol-3-one (11)

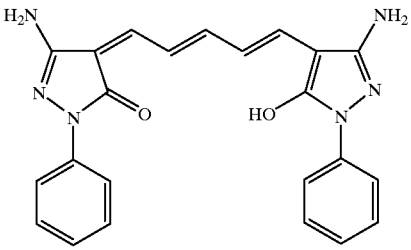

5-Amino-4-(5-(3-amino-5-hydroxy-1-phenyl-1H-pyrazol-4-yl)-penta-2,4-dienyliden)-2-phenyl-2,4-dihydropyrazol-3-one (12)

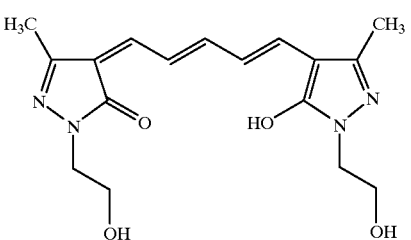

2-(2-Hydroxyethyl)-4-(5-(5-hydroxy-1-(2-hydroxyethyl)-3-methyl-1H-pyrazol-4-yl)-penta-2,4-dienyliden)-5-methyl-2,4-dihydro-pyrazol-3-one (13)

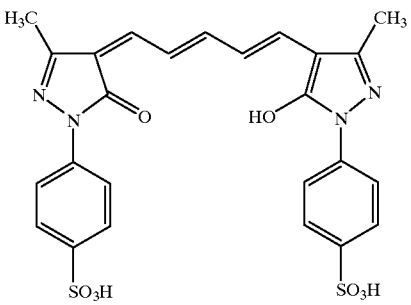

4-(5-(5-Hydroxy-3-methyl-1-(4-sulfophenyl)-1H-pyrazol-4-yl)-penta-2,4-dienyliden)-5-methyl-2-(4-sulfophenyl)-2,4-dihydropyrazol-3-one (14)

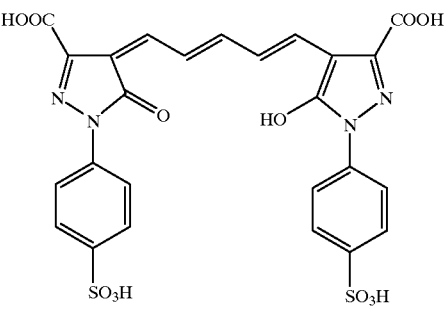

4-(5-(3-Carboxy-5-oxo-1-(4-sulfophenyl)-1,5-dihydropyrazol-4-yliden)-penta-1,3-dienyl)-5-hydroxy-1-(4-sulfophenyl)-1H-pyrazol-3-carboxylic acid (15)

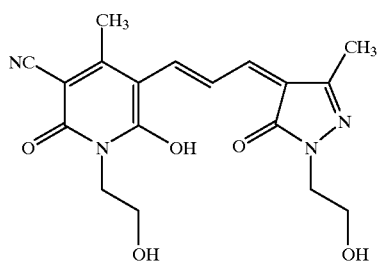

6-Hydroxy-1-(2-hydroxyethyl)-5-(3-(1-(2-hydroxyethyl)-3-methyl-5-oxo-1,5-dihydro-pyrazol-4-yliden)-propenyl)-4-methyl-2-oxo-1,2-dihydro-pyridin-3-carbonitrile (16)

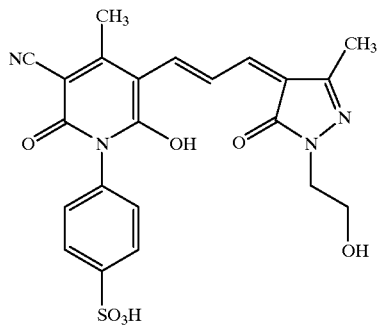

6-Hydroxy-5-(3-(1-(2-hydroxyethyl)-3-methyl-5-oxo-1,5-dihydro-pyrazol-4-yliden)-propenyl)-4-methyl-2-oxo-1-(4-sulfophenyl)-1,2-dihydro-pyridin-3-carbonitrile (17)

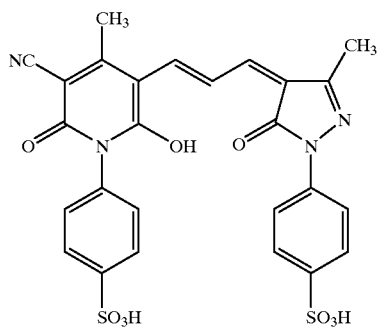

6-Hydroxy-4-methyl-5-(3-(3-methyl-5-oxo-1-(4-sulfophenyl)-1,5-dihydropyrazol-4-yliden)-propenyl)-2-oxo-1-(4-sulfophenyl)-1,2-dihydro-pyridin-3-carbonitrile (18)

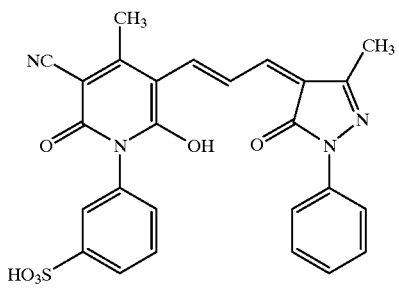

6-Hydroxy-4-methyl-5-(3-(3-methyl-5-oxo-1-phenyl-1,5-dihydropyrazol-4-yliden)-propenyl)-2-oxo-1-(3-sulfophenyl)-1,2-dihydropyridin-3-carbonitrile (19)

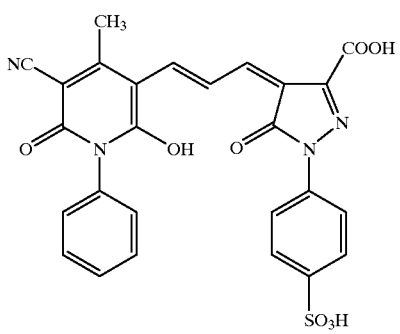

4-(3-(5-Cyano-2-hydroxy4-methyl-6-oxo-1-phenyl-1,6-dihydropyridin-3-yl)-allyliden)-5-oxo-1-(4-sulfophenyl)-4,5-dihydro-1H-pyrazol-3-carboxylic acid (20)

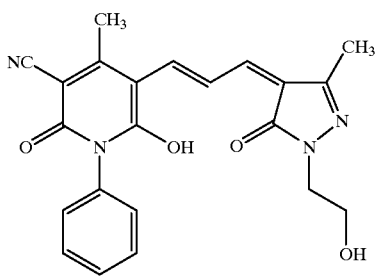

6-Hydroxy-5-(3-(1-(2-hydroxyethyl)-3-methyl-5-oxo-1,5-dihydropyrazol-4-yliden)-propenyl)-4-methyl-2-oxo-1-phenyl-1,2-dihydropyridin-3-carbonitrile (21)

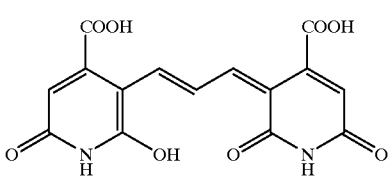

5-(3-(4-Carboxy-2,6-dioxo-1,6-dihydro-2H-pyridin-3-yliden)-propenyl)-6-hydroxy-2-oxo-1,2-dihydropyridin-4carboxylic acid (22)

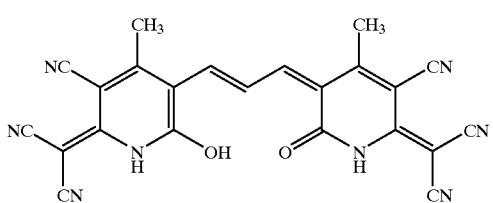

2-(3-Cyano-5-(3-(5-cyano-6-dicyanomethylen-4-methyl-2-oxo-1,6-dihydro-2H-pyridin-3-yliden)-propenyl)-6-hydroxy-4-methyl-1H-pyridin-2-yliden)-malononitrile (23)

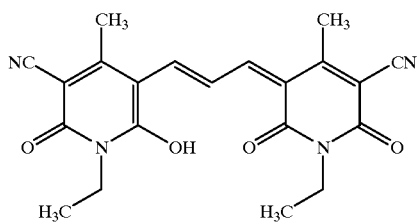

5-(3-(5-Cyano-1-ethyl-4-methyl-2,6-dioxo-1,6-dihydro-2H-pyridin-3-yliden)-propenyl)-1-ethyl-6-hydroxy-4-methyl-2-oxo-1,2-dihydropyridin-3-carbonitrile (24)

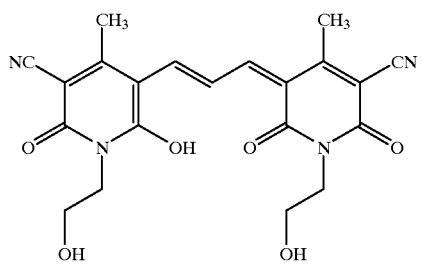

5-(3-(5-Cyano-1-(2-hydroxyethyl)-4-methyl-2,6-dioxo-1,6-dihydro-2H-pyridin-3-yliden)-propenyl)-6-hydroxy-1-(2-hydroxyethyl)-4-methyl-2-oxo-1,2-dihydropyridin-3-carbonitrile (25)

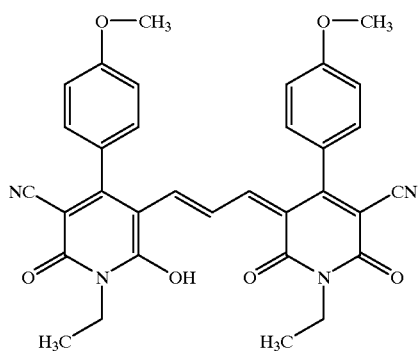

5-(3-(5-Cyano-1-ethyl-4-(4-methoxyphenyl)-2,6-dioxo-1,6-dihydro-2H-pyridin-3-yliden)-propenyl)-1-ethyl-6-hydroxy-4-(4-methoxyphenyl)-2-oxo-1,2-dihydropyridin-3-carbonitrile (26)

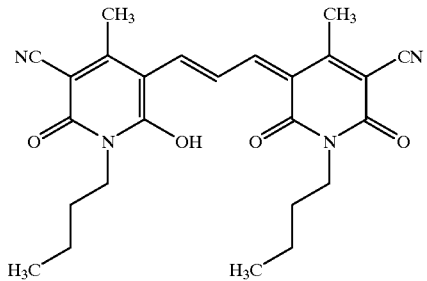

1-Butyl-5-(3-(1-butyl-5-cyano-4-methyl-2,6-dioxo-1,6-dihydro-2H-pyridin-3-yliden)-propenyl)-6-hydroxy-4-methyl-2-oxo-1,2-dihydropyridin-3-carbonitrile (27)

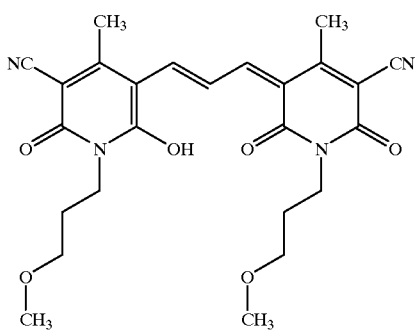

5-(3-(5-Cyano-1-(3-methoxy-propyl)4-methyl-2,6-dioxo-1,6-dihydro-2H-pyridin-3-yliden)-propenyl)-6-hydroxy-1-(3-methoxy-propyl)-4-methyl-2-oxo-1,2-dihydropyridin-3-carbonitrile (28)

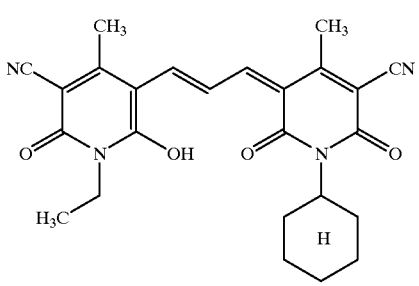

5-(3-(5-Cyano-1-cyclohexyl-4-methyl-2,6-dioxo-1,6-dihydro-2H-pyridin-3-yliden)-propenyl)-1-ethyl-6-hydroxy-4-methyl-2-oxo-1,2-dihydropyridin-3-carbonitrile (29)

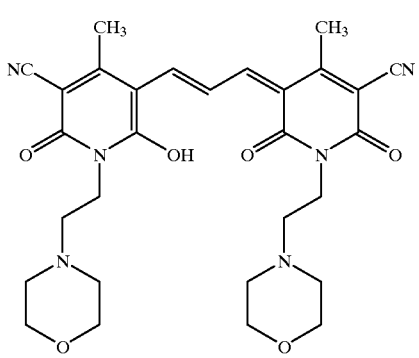

5-(3-(5-Cyano-4-methyl-1-(2-morpholin-4-yl-ethyl)-2,6-dioxo-1,6-dihydro-2H-pyridin-3-yliden)-propenyl)-6-hydroxy-4-methyl-1-(2-morpholin-4-yl-ethyl)-2-oxo-1,2-dihydropyridin-3-carbonitrile (30)

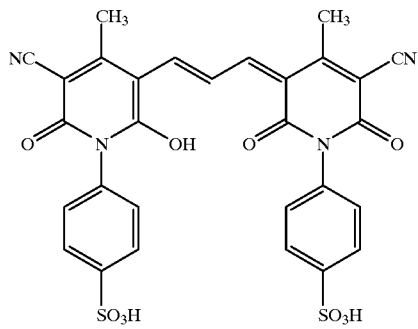

5-(3-(5-Cyano-4-methyl-2,6-dioxo-1-(4-sulfophenyl)-1,6-dihydro-2H-pyridin-3-yliden)-propenyl)-6-hydroxy-4-methyl-2-oxo-1-(4-sulfophenyl)-1,2-dihydropyridin-3-carbonitrile (31)

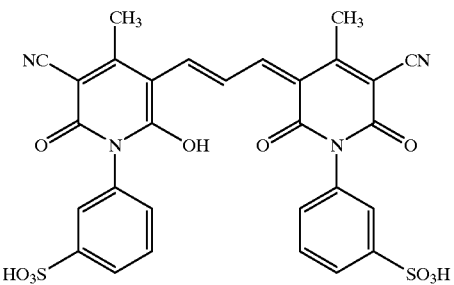

5-(3-(5-Cyano-4-methyl-2,6-dioxo-1-(3-sulfophenyl)-1,6-dihydro-2H-pyridin-3-yliden)-propenyl)-6-hydroxy-4-methyl-2-oxo-1-(3-sulfophenyl)-1,2-dihydropyridin-3-carbonitrile (32)

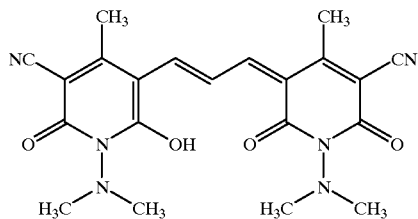

5-(3-(5-Cyano-1-dimethylamino-4-methyl-2,6-dioxo-1,6-dihydro-2H-pyridin-3-yliden)-propenyl)-1-dimethylamino-6-hydroxy-4-methyl-2-oxo-1,2-dihydropyridin-3-carbonitrile (33)

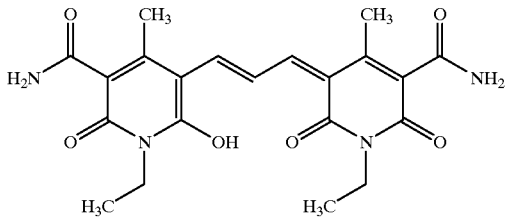

5-(3-(5-Carbamoyl-1-ethyl-4-methyl-2,6-dioxo-1,6-dihydro-2H-pyridin-3-yliden)-propenyl)-1-ethyl-6-hydroxy-4-methyl-2-oxo-1,2-dihydropyridin-3-carboxamide (34)

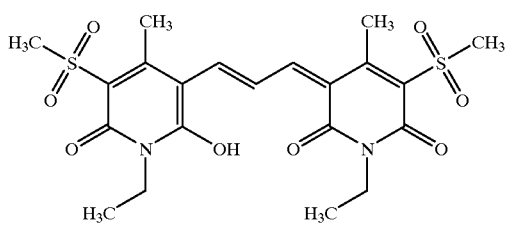

1-Ethyl-3-(3-(1-ethyl-2-hydroxy-5-methansulfonyl-4-methyl-6-oxo-1,6-dihydro-pyridin-3-yl)-allyliden)-5-methansulfonyl-4-methyl-3H-pyridin-2,6-dione (35)

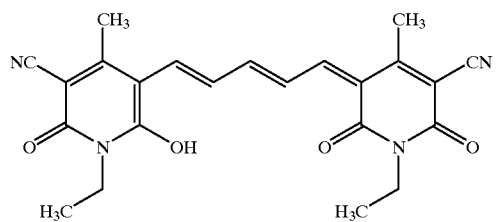

5-(5-(5-Cyano-1-ethyl-4-methyl-2,6-dioxo-1,6-dihydro-2H-pyridin-3-yliden)-penta-1,3-dienyl)-1-ethyl-6-hydroxy-4-methyl-2-oxo-1,2-dihydropyridin-3-carbonitrile (36)

Preferred among the aforesaid dyes are, in particular the compounds of formula (II) to (IV) wherein R1 and R1' are equal and denote a phenyl, sulfophenyl, methyl or hydroxyethyl group, R2 and R2' are equal and denote hydrogen, a methyl, carboxyl, carboxylate ester or amino group, R3 and R3' independently of each other denote hydrogen or a straight-chain C1 to C4 alkyl group, a methoxy, hydroxyethyl, sulfoethyl, phenyl or sulfophenyl group, R4 and R4' are equal and denote hydrogen, or a nitrile or carboxamido group, R6 denotes a phenyl, sulfophenyl, methyl or hydroxyethyl group, R7 denotes hydrogen, or a methyl, carboxyl, carboxylate ester or amino group, R8 denotes hydrogen or a straight-chain C1 to C4 alkyl group, a methoxyethyl, hydroxyethyl, sulfoethyl, phenyl or sulfophenyl group, R9 denotes a nitrile group, R10 denotes a methyl or carboxyl group, Z denotes oxygen, R denotes a hydrogen atom or a methyl group, and the indices m and n equal 0, 1 or 2, the sum of m and n having a maximum value of 2.

In the case of dyes with a pronounced anionogenic character (this is true primarily for dyes containing acid functions such as sulfonic acid or carboxyl groups), the dyes can be used also in the form of their physiologically tolerated salts. Suitable, in particular, are the following compounds.

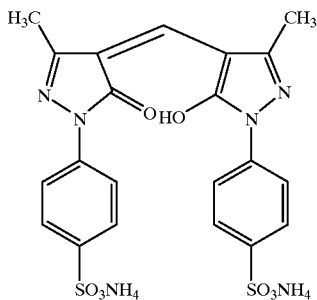

Diammonium-4-(5-hydroxy-3-methyl-1-(4-sulfophenyl)-1H-pyrazol-4-yl-methylen)-5-methyl-2-(4-sulfophenyl)-2,4-dihydro-pyrazol-3-one (3a)

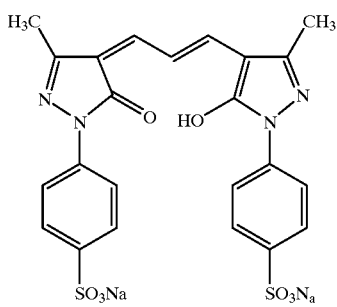

Disodium 4-(3-(5-hydroxy-3-methyl-1-(4-sulfophenyl)-1H-pyrazol-4-yl)-allyliden)-5-methyl-2-(4-sulfophenyl)-2,4-dihydro-pyrazol-3-one (7a)

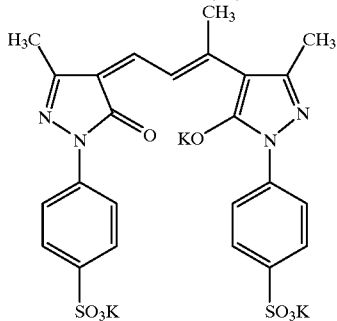

Tripotassium 4-(3-(5-hydroxy-3-methyl-1-(4-sulfophenyl)-1H-pyrazol-4-yl)-but-2-enyliden)-5-methyl-2-(4-sulfophenyl)-2,4-dihydro-pyrazol-3-one (8a)

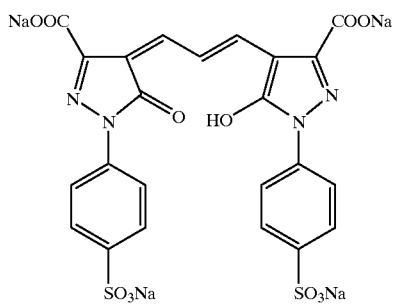

Tetrasodium 4-(3-(3-Carboxy-5-oxo-1-(4-sulfophenyl)-1,5-dihydropyrazol-4-yliden)-propenyl)-5-hydroxy-1-(4-sulfophenyl)-1H-pyrazol-3-carboxylic acid (9a)

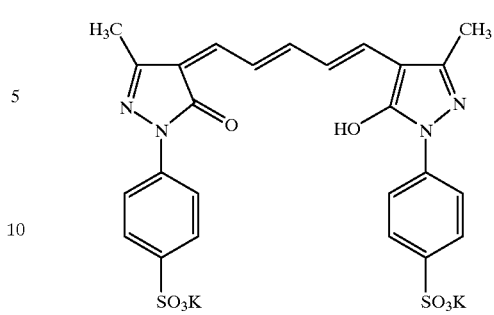

Dipotassium 4-(5-(5-Hydroxy-3-methyl-1-(4-sulfophenyl)-1H-pyrazol-4-yl)-penta-2,4-dienyliden)-5-methyl-2-(4-sulfophenyl)-2,4-dihydropyrazol-3-one (14a)

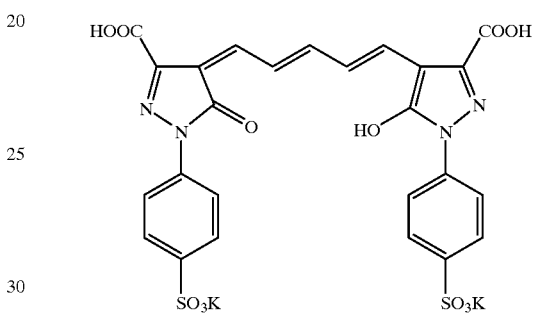

Dipotassium 4-(5-(3-carboxy-5-oxo-1-(4-sulfo-phenyl)-1,5-dihydro-pyrazol-4-yliden)-penta-1,3-dienyl)-5-hydroxy-1-(4-sulfo-phenyl)-1H-pyrazol-3-carboxylic acid (15a)

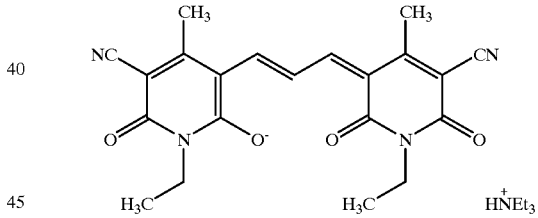

Triethylammonium-5-(3-(5-cyano-1-ethyl-4-methyl-2,6-dioxo-1,6-dihydro-2H-pyridin-3-yliden)-propenyl)-1-ethyl-6-hydroxy-4-methyl-2-oxo-1,2-dihydro-pyridin-3-carbonitrile (24a)

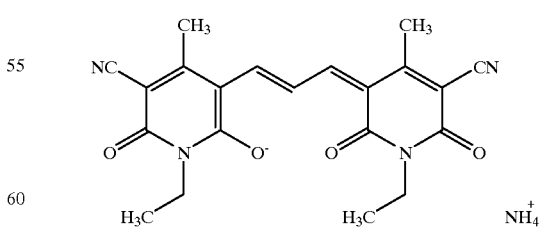

Ammonium 5-(3-(5-cyano-1-ethyl-4-methyl-2,6-dioxo-1,6-dihydro-2H-pyridin-3-yliden)-propenyl)-1-ethyl-6-hydroxy-4-methyl-2-oxo-1,2-dihydro-pyridin-3-carbonitrile (24b)

The total amount of dyes of formula (Ia)(Ib) or (II) to (IV) in the colorants according to the invention for coloring keratin dyes is from 0.01 to 5 wt % and preferably from 0.5 to 4 wt %.

The colorants according to the invention also contain at least one natural or synthetic nonoxidative dye. Suitable synthetic nonoxidative dyes are, for example, the nitro, azo, triphenylmethane, quinone, anthraquinone or acid dyes, particularly

- 1,4-bis-[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(hydroxyethyl)amino-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino-2-nitrobenzene (HC Blue No. 11), 1-[2,3-dihydroxypropyl)amino-4-[methyl-2-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-[(4-amino-2-nitrophenyl)amino]-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol hydrochloride, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxpropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)-amino-3-nitrobenzene (HC Yellow No. 12), 4-[(2-hydroxyethyl)amino-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15, 1,4-di[(2,3-dihydroxypropyl)amino]-9,10-anthraquinone, 1-[(2-hydroxyethyl)amino]-4-methylamino-9,10-anthraquinone (C.I. 61505, Disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I. 62015, Disperse Red No. 11, Solvent Violet No. 26), 1,4-dihydroxy-5,8-bis-[(2-hydroxyethyl)amino]-9,10-anthraquinone (C.I. 62500, Disperse Blue No. 7, Solvent Blue No. 69), 1-[(di(2-hydroxyethyl)amino]-3-methyl-4-[(4-nitrophenyl)azo]benzene (C.I. 11210, Disperse Red No. 17), 4-[(4-aminophenyl)azo]-1-[di(2-hydroxyethyl)amino]-3-methylbenzene (HC Yellow No. 7), 2,6-diamino-3-[(pyridin-3-yl)azo)pyridine, 6-hydroxy-5-[(4-sulfophenyl)azo]-2-naphthalenesulfonic acid disodium salt (C.I. 15985; Food Yellow No. 3; FD&C Yellow No. 6), 2,4-dinitro-1-naphthol-7-sulfonic acid disodium salt (C.I. 10316; Acid Yellow No. 1); Food Yellow No. 1), 2-(indan-1, 3-dione-2-yl)quinoline-x,x-sulfonic acid (mixture of mono and disulfonic acid) (C.I. 47005; D&C Yellow No. 5; Food Yellow No. 13); Acid Yellow No. 3), 5-hydroxy-1-(4-sulfophenyl)-[(4-[(4-sulfophenyl)azo]pyrazole-3-carboxylic acid trisodium salt (C.I. 19140; Food Yellow No. 4; Acid Yellow No. 23), 9-(2-carboxyphenyl)-6-hydroxy-3H-xanthen-3-one (C.I. 45350; Acid Yellow No. 73; D&C Yellow No. 8), 5-[(2,4-dinitrophenyl)amino]-2-phenylaminobenzenesulfonic acid sodium salt (C.I. 10385; Acid Orange No. 3), 4-[(2,4-dihydroxyphenyl)axo]benzenesulfonic acid monosodium salt (C.I. 14270; Acid Orange No. 6), 4-[(2-hydroxy-1-naphthyl)azo)benzenesulfonic acid sodium salt (C.I. 15510; Acid Orange No. 7), 4-[(2,4-dihydroxy-3-[(2,4-dimethylphenyl)azo]phenyl)azo]benzenesulfonic acid sodium salt (C.I. 20170; Acid Orange No. 24), 4-hydroxy-3-[(4-sulfo-1-naphthyl)azo]-1-naphthalenesulfonic acid disodium salt (C.I. 14720; Acid Red No. 14), 6-hydroxy-5-[(4-sulfo-1-naphthyl)azo-2,4-naphthalenedisulfonic acid trisodium salt (C.I. 16255; Ponceau 4R; Acid Red No. 18), 3-hydroxy-4-[(4-sulfo-1-naphthyl)azo]-2,7-naphthalenedisulfonic acid trisodium salt (C.I. 16185; Acid Red No. 27), 8-amino-1-hydroxy-2-(phenylaxo)-3,6-naphthalenedisulfonic acid disodium salt (C.I. 17200; Acid Red No. 33), 5-(acetylamino)-4-hydroxy-3-[(2-methylphenyl)azo]-2,7-naphthalenedisulfonic acid disodium salt (C.I. 18065; Acid Red No.35), 2-(3-hydroxy-2,4,5,7-tetraiododibenzopyran-6-one-9-yl) benzoic acid disodium salt (C.I. 45430; Acid Red No. 51), N-[6-(diethylamino)-9-(2,4-disulfophenyl)-3H-xanthen-3-ylidene-N-ethylethaneammonium hydroxide, inner salt, sodium salt (C.I. 45100; Acid Red No. 52), 8-[(4-(phenyl-azo) phenyl)azo]-7-naphthol-1,3-disulfonic acid disodium salt (C.I. 27290; Acid Red No. 73), 2',4',5',7'-tetrabromo-3',6'-dihydroxyspiro[isobenzofuran-1(3H),-9'[9H]xanthene-3-one disodium salt (C.I. 45380; Acid Red No. 87), 2',4',5',7'-tetrabromo-4,5,6,7-tetrachloro-3', 6'-dihydroxyspiro[isobenzofuran 1(3H),9'[9H] xanthene]-3-one disodium salt (C.I. 45410; Acid Red No. 92), 3',6'-dihydroxy-4',5'-diiodospiro [isobenzofuran-1(3H),9'(9H)-xanthene]-3-one disodium salt (C.I. 45425; Acid Red No.95), (2-sulfophenyl)-di-[4-(ethyl((4-sulfophenyl) methyl)-amino) phenyl]carbenium disodium salt, betaine (C.I. 42090; Acid Blue No. 9; FD&C Blue No. 1), 1,4-bis-[(2-sulfo-4-methylphenyl)amino]-9,10-anthraquinone disodium salt (C.I. 61570; Acid Green No. 25), bis-[4-dimethylamino)phenyl]-(3,7-disulfo-2-hydroxy-1-naphthyl)carbenium inner salt, monosodium salt (C.I. 44090; Food Green No. 4; Acid Green No. 50), bis-[4-(diethylamino)phenyl]-(2,4-disulfophenyl) carbenium inner salt, sodium salt (2:1) (C.I. 42045; Food Blue No. 3; Acid Blue No. 1), bis-[4-(diethylamino)phenyl](5-hydroxy-2,4-disulfophenyl) carbenium inner salt, calcium salt (2:1) (C.I. 42051; Acid Blue No. 3), 1-amino-4-(cyclohexylamino)-9,10-anthraquinone-2-sulfonic acid sodium salt (C.I. 62045; Acid Blue No. 62), 2-(1,3-dihydro-3-oxo-5-sulfo-2H-indol-2-ylidene)-2,3-dihydro-3-oxo-1H-indol-5-sulfonic acid disodium salt (C.I. 73015; Acid Blue No. 74), 9-(2-carboxy-phenyl)-3-[(2-methylphenyl) amino]-6-[(2-methyl-4-sulfophenyl)amino]xanthylium inner salt, monosodium salt (C.I. 45190; Acid Violet No.9), 1-hydroxy-4-[(4-methyl-2-sulfophenyl)amino]-9,10-anthraquinone sodium salt (C.I. 60730; D&C Violet No.2; Acid Violet No. 43), bis-[3-nitro-4-[(4-phenylamino)-3-sulfophenylamino]phenyl]sulfone (C.I. 10410; Acid Brown No. 13), 5-amino-4-hydroxy-6-[(4-nitrophenyl)azo]-3-(phenylazo)-2,7-naphthalenedisulfonic acid disodium salt (C.I. 20470; Acid Black No. 1), 3-hydroxy-4-[(2-hydroxy-1-naphthyl)azo-7-nitro-1-naphthalenesulfonic acid chromium complex (3:2) (C.I. 15711; Acid Black No.52), 3-[(2,4-dimethyl-5-sulfophenyl)azo]-4-hydroxy-1-naphthalenesulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl)azo]-1-naphthyl)azo]-1,7-naphthalenedisulfonic acid tetrasodium salt (C.I. 28440; Food Black No.1) and 3-hydroxy-4-(3-methyl-5-oxo-1-phenyl-4,5-dihydro-1H-pyrazol-4-ylazo) naphthalene-1-sulfonic acid sodium salt chromium complex (Acid Red No. 195).

Although the polymethine dyes contained in the colorant according to the invention are by definition anionic in nature, some of these dyes, particularly monomethine oxonols (1) and (2) are, surprisingly, fully compatible with cationic ("basic") dyes, for example 9-(dimethylamino) benzo[a]phenoxazin-7-ium chloride (C.I. 51175; Basic Blue No. 6), di[4-diethylamino)phenyl][4-(ethylamino) naphthyl]-carbenium chloride (C.I. 42595; Basic Blue No. 7), 3,7-di(dimethylamino)phenothiazin-5-ium chloride, (C.I. 52015; Basic Blue No. 9), di[4-(dimethylamino) phenyl][4-(phenylamino)naphthyl]carbenium chloride (C.I. 44045); Basic Blue 26), 2-[4-(ethyl(2-hydroxyethyl)amino) phenyl)axo]-6methoxyoxy-3-methylbenzothiazolium methylsulfate (C.I. 11154; Basic Blue 41), 8-amino-2-bromo-5-hydroxy-4-imino-6-[(3-(trimethylammonio)phenyl)amino]-1(4H)-naphthalenone chloride (C.I. 56059; Basic Blue No. 99), bis[4-(dimethylamino)phenyl][4-(methylamino) phenyl]carbenium chloride (C.I. 42535, Basic Violet No. 1), tris-[4-(dimethylamino)phenyl]carbenium chloride (C.I. 42555; Basic Violet No. 3), 2-[3,6-diethylamino) dibenzopyranium-9-yl benzoic acid chloride (C.I. 45170; Basic Violet No. 10), di(4-aminophenyl)-(4-amino-3-methylphenyl)carbenium chloride (C.I. 42510; Basic Violet No. 14), 1,3-bis[(2,4-diamino-5-methylphenyl)azo]-3-methylbenzene (C.I. 21010, Basic Brown No. 4), 1-[(4-aminophenyl)azo-7-(trimethylammonio)-2-naphthol chloride (C.I. 12250, Basic Brown No. 16), 1-[(4-aminophenyl) azo-7-(trimethylammonio)-2-naphthol chloride (C.I. 12250, Basic Brown No. 16), 1-[(4-amino-2-nitrophenyl)azo]-7-(trimethylammonio)-2-naphthol chloride (Basic Brown No. 17),1-[(4-amino-3-nitrophenyl)azo]-7-(trimethylammonio)-2-naphthol chloride (C.I. 12251; Basic Brown No. 17) [sic—Translator], 3,7-diamino-2,8-dimethyl-5-phenylphenazinium chloride (C.I. 50240; Basic Red No. 2), 1,4-dimethyl-5-[(4-(dimethylamino)phenyl)azo]-1,2,4-triazolium chloride (C.I. 11055; Basic Red No. 22), 2-hydroxy-1[(2-methoxyphenyl)azo-7-(trimethylammonio) naphthalene chloride (C.I. 12245; Basic Red No. 76), 2-[2-(2,4-dimethoxyphenyl)amino)ethenyl]-1,3,3-trimethyl-3H-indol-1-ium chloride (C.I. 48055; Basic Yellow No. 11), 3-methyl-1-phenyl-4-[(3-(trimethylammonio)phenyl)azo] pyrazol-5-one chloride (C.I. 12719; Basic Yellow No. 57) or bis-[4-(diethylamino)phenyl]phenylcarbenium hydrogen sulfate (1:1) (C.I. 42040; Basic Green No: 1).

The total amount of natural or synthetic nonoxidative dyes contained in the colorant according to the invention is from 0.01 to 15 wt % and particularly from 0.1 to 12 wt %.

To increase the color intensity, conventional carriers used in cosmetic systems can be employed. Suitable compounds are, for example, benzyl alcohol, furfuryl alcohol, 2-hydroxymethylthiophene, vanillin or isovanillin. Other suitable carriers are described in German Unexamined Patent Application DE 196 18 595, the disclosures of which are hereby incorporated by reference.

The colorants according to the invention for tinting keratin fibers can be used in the form of, for example, a solution, particularly an aqueous-alcoholic solution, or a cream, gel or emulsion. Suitable solvents besides water are, for example the lower aliphatic monohydric or polyhydric alcohols, the esters and ethers thereof or mixtures of said solvents with each other or with water. The maximum boiling point of the aforesaid suitable solvents is about 400° C., a boiling point from 20° C. to 250° C. being preferred.

It is also possible to dispense said colorants by means of an atomizer or some other suitable pumping or spraying device or, in admixture with conventional propellants liquefied under pressure, dispense them from a pressurized container in the form of an aerosol spray or aerosol foam.

The pH of the colorants according to the invention is from 2 to 11, a pH from 2.5 to 8 being particularly preferred. An alkaline pH is preferably obtained with ammonia, but an organic amine, for example monoethanolamine or triethanolamine, can be used in place of ammonia. To obtain an acidic pH, on the other hand, an organic or inorganic acid, for example hydrochloric, sulfuric, phosphoric, ascorbic, glycolic or lactic acid, can be used.

Naturally, the aforedescribed colorants can optionally contain other common additives suitable for keratin fiber colorants, for example hair-care agents, wetting agents, thickeners, softeners, preservatives and perfumes as well as other additives listed in the following.

The colorants according to the invention can also contain wetting agents or emulsifiers from the classes of anionic, amphoteric, nonionic or zwitterionic surface-active agents, such as fatty alcohol sulfates, alkanesulfonates, alkylbenzenesulfonates, alkylbetaines, α-olefinsulfonates, ethoxylated fatty alcohols, ethoxylated nonylphenols, fatty alkanolamines, ethoxylated fatty esters, fatty alcohol polyglycol ether sulfates, alkyl polyglucosides, thickeners such as the higher fatty alcohols, starch, alginates, bentonites, cellulose derivatives, vaseline, paraffin oil and fatty acids, water-soluble polymeric thickeners such as various types of natural gum, guar gum, xanthan gum, carob bean flour, pectin, dextran, agar, amylose, amylopectin, dextrins, clays, or fully synthetic hydrocolloids, such as polyvinyl alcohol, furthermore hair-care agents such as lanolin derivatives, cholesterol, pantothenic acid, water-soluble polymers, protein derivatives, provitamins, vitamins, plant extracts, sugar and betaine, auxiliary agents such as humectants, electrolytes, antioxidants, fatty amides, sequestrants, film-forming agents and preservatives.

The aforedescribed colorants can also contain natural or synthetic polymers or modified natural polymers whereby the keratin fiber is strengthened while it is being colored. Such agents are generally referred to as shade or color enhancers. Suitable among the synthetic polymers known to be used in cosmetics for this purpose are, for example, polyvinylpyrrolidone, polyvinyl acetate, polyvinyl alcohol, or polyacrylic compounds, such as polyacrylic acid or polymethacrylic acid, polyacrylonitrile, polyvinyl acetates and copolymers of such compounds, for example polyvinylpyrrolidone-vinyl acetate copolymers. Suitable natural or modified natural polymers are, for example, chitosan, (deacetylated chitin) or chitosan derivatives.

The said constituents are used in amounts that are normal for such purposes. For example, the wetting agents and emulsifiers are used in an amount of about 0.5 to 30 wt %, the thickeners in an amount from about 0.1 to 25 wt % and the hair-care agents in an amount from about 0.1 to 5 wt %. The aforesaid polymers can be used in the colorants of the invention in amounts that are normal for such colorants, particularly in an amount from about 1 to 5 wt %.

The keratin fiber colorants of the invention are particularly well suited for the coloring of hair. For this purpose, the colorants of the invention are applied to the hair in the usual manner in an amount sufficient for hair coloring and, in general, in an amount from about 50 to 150 grams. After an exposure time sufficient for hair coloring, usually about 10 to 45 min at 20° to 50° C. and preferably 15 to 30 min at about 40° C., the hair is rinsed with water, optionally washed with a shampoo and/or an aqueous solution of a weak organic acid, for example citric or tartaric acid, again rinsed and then dried.

The colorants with the additional strengthening action are used in the known and conventional manner by wetting the hair with them, styling the hair and then drying.

As regards the range of possible coloring, the hair colorants according to the invention can give rise to a broad spectrum of different shades ranging from natural colors to highly fashionable bright shades, depending on the type and composition of the dyes used. The advantageous properties of the novel colorants manifest themselves particularly on light-damaged and weather-damaged or permanently waved hair. In particular, the resulting tints are characterized by very good stability and wash-out resistance.

The monomethine oxonol dyes (m=n=0) can be prepared from the corresponding heterocyclic compounds and trialkyl orthoesters or formamides as bridge precursors. Numerous compounds are described by B. Schied, J. prak. Chem 157, page 203 ff (1941) and by S. Hünig, Annalen 574, page 106 ff (1951) as well in the literature cited therein. According to German Unexamined Patent Application DE 20 12 050, the trimethine oxonols (m+n=1) can be prepared from tetramethoxypropane, trimethoxypropene or malonaldehyde dianil. The pentamethine oxonols (m+n=2) can be prepared from N-acceptor-substituted pyridinium salts by opening the pyridine ring ("Zincke cleavage") or from an appropriate derivative, for example glutaconaldehyde dianil. A complete review of this subject can be found in Houben-Weyl 7/1, 4th edition (1954) on pages 263 ff and in the literature cited therein.

The following examples are intended to illustrate the object of the invention in greater detail without limiting it to these examples.

EXAMPLES

Example 1

Method for Preparing 2-(2-Hydroxyethyl)-4-(5-hydroxy-1-(2-hydroxyethyl)-3-methyl-1H-pyrazol-4-ylmethylene)-5-methyl-2,4-dihydropyrazol-3-one (2)

17 g of 1-(2-hydroxyethyl)-3-methyl-1H-pyrazole and 7 g of trimethyl orthoformate were allowed to reflux in 50 mL of pyridine. After 15 hours, the mixture was cooled and the precipitate was filtered off. Recrystallization from 220 mL of ethanol gave 9.5 g of 2-(2-hydroxyethyl)-4-(5-hydroxy-1-(2-hydroxyethyl)-3-methyl-1H-pyrazol-4-ylmethylene)-5-methyl-2,4-dihydropyrazol-3-one (2) in the form of shiny yellow needles.

| Melting point: | | 212–214° C. | |
| --- | --- | --- | --- |
| $\lambda_{max}$ (H$_2$O): | | 404 nm | |
| $\epsilon$: | | 55,200 | |
| Elemental analysis: | | | |
| (C$_{13}$H$_{18}$N$_4$O$_4$) | C | H | N |
| Calcd. | 53.05% | 6.16% | 19.04% |
| Found | 53.04% | 6.15% | 19.11% |

Example 2

Method for Preparing Ammonium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile (24b)

(a) 26.5 g of 5-(3-(5-cyano-1-ethyl-4-methyl-2,6-dioxo-1,6-dihydro-2H-pyridin-3-ylidene)propenyl-1-ethyl-6-hydroxy-4-methyl-2-oxo-1,2-dihydropyridine-3-carbonitrile and 5.2 g of ammonium acetate in 250 mL of acetic acid were heated at 80° C. for 2 hours. This gave a thick dye suspension. The dye suspension was then cooled, and the dye was filtered off and dried. This gave 25.5 g of ammonium 5-(3-(5-cyano-1-ethyl-4-methyl-2, 6-dioxo-1,6-dihydro-2H-pyridin-3-ylidene)propenyl)-1-ethyl-6hydroxy-4-methyl-2-oxo-1,2-dihydropyridine-3-carbonitrile (24b).

| Melting point: | | 300–301° C. | |
| --- | --- | --- | --- |
| $\lambda_{max}$ (methanol): | | 596 nm | |
| $\epsilon$ | | 177,500 | |
| Elemental analysis: | | | |
| C$_{21}$H$_{20}$N$_4$O$_4$ × NH$_3$ | C | H | N |
| Calcd. | 61.50% | 5.66% | 17.11% |
| Found | 61.53% | 5.79% | 17.07% |

(b) 4.9 g of commercial triethylammonium 5-(3-(5-cyano-1-ethyl-4-methyl-2,6-dioxo-1,6-dihydro-2H -pyridin-3- ylidene)propenyl-1-ethyl-6-hydroxy-4-methyl-2-oxo-1,2-dihydropyridine-3-carbonitrile (24a) was made to react with 0.8 g of ammonium acetate in 75 mL of acetic acid as described under (a). This gave 3.6 g of dye (24a).

Example 3

Colorant

| | |
|---|---|
| 0.7 g | of 2-(2-hydroxyethyl)-4-(5-hydroxy-1-(2-hydroxyethyl)-3-methyl-1 H-pyrazol-4-ylmethylene)-5-methyl-2,4-dihydropyrazol-3-one (2) |
| 0.6 g | of 1-[(2-hydroxyethyl)amino]-4-methylamino-9,10-anthraquinone (C.I. 61505, Disperse Blue No. 3) |
| 20.0 g | of ethanol |
| to 100.0 g | water, demineralized |

The foregoing colorant solution was applied to bleached hair. After an exposure time of 20 min at 40° C., the hair was washed with water and dried. The hair color was of a blue-green shade. After the washing test, a slight color loss, particularly of the conventional direct dye (Disperse Blue No. 3), was observed visually.

| | $L^*$ | $a^*$ | $b^*$ | $\Delta E_{1/2}$ | Color loss, % |
|---|---|---|---|---|---|
| Untreated hair | 84, 80 | −0, 75 | 11, 53 | | |
| Colored hair | 36, 30 | −12, 60 | −8, 04 | 53, 63 | |
| 5x washed and dried hair | 42, 28 | −15, 09 | −5, 56 | 6, 94 | 13 |

Example 4

Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 1.7 g | of triethylammonium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile (24a) |
| 1.5 g | of 6-hydroxy-5-[(4-sulfo-1-naphthyl)azo]-2,4-napthalenedisulfonic acid trisodium salt (C.I. 16255; Acid Red No. 18) |
| to 100.0 g | water, demineralized. |

The foregoing colorant solution was applied to bleached hair. After an exposure time of 20 min at 40° C., the hair was washed with water and dried. The hair color was of a blue-violet shade.

After the washing test, no color loss was observed visually.

| | $L^*$ | $a^*$ | $b^*$ | $\Delta E_{1/2}$ | Color loss, % |
|---|---|---|---|---|---|
| Untreated hair | 84, 80 | −0, 75 | 11, 53 | | |
| Colored hair | 20, 48 | 18, 23 | −25, 38 | 76, 55 | |
| 5x washed and dried hair | 22, 71 | 21, 44 | −27, 47 | 4, 43 | 6 |

Example 5

Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 1.4 g | of disodium 4-(3-(5-hydroxy-3-methyl-1-(4-sulfophenyl)-1H-pyrazol-4-yl)-allylidene)-5-methyl-2-(4-sulfophenyl)-2,4-dihydropyrazol-3-one (7a) |
| 0.5 g | of 4-[(2-hydroxyethyl)amino]-3-nitro-1-methylbenzene |
| to 100.0 g | water, demineralized |

The foregoing colorant solution was applied to bleached hair. After an exposure time of 20 min at 40° C., the hair was washed with water and dried. The hair color was of a vivid red shade. After the washing test, no color loss was observed visually.

| | $L^*$ | $a^*$ | $b^*$ | $\Delta E_{1/2}$ | Color loss, % |
|---|---|---|---|---|---|
| Untreated hair | 84, 80 | −0, 75 | 11, 53 | | |
| Colored hair | 39, 39 | 65, 56 | 36, 61 | 84, 19 | |
| 5x washed and dried hair | 39, 51 | 66, 38 | 37, 32 | 1, 09 | 1 |

Example 6

Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 1.8 g | of dipotassium 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazole-3-carboxylic acid (15a) |
| 0.1 g | of 5-chloro-1,4-[di(2,3-dihydroxypropyl)amino]-2-nitrobenzene (HC Red No. 11) |
| to 100.0 g | water, demineralized |

The foregoing colorant solution was applied to bleached hair. After an exposure time of 20 min at 40° C., the hair was washed with water and dried. The hair color was of a dark egg plant shade. After the washing test, no color loss was observed visually.

|  | L* | a* | b* | $\Delta E_{1/2}$ | Color loss, % |
|---|---|---|---|---|---|
| Untreated hair | 84.80 | −0.75 | 11.53 |  |  |
| Colored hair | 18.43 | 2.83 | −2.39 | 67.91 |  |
| 5× washed and dried hair | 21.35 | 3.37 | −3.87 | 3.32 | 5 |

Example 7

Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 0.7 g | of 2-(2-hydroxyethyl)-4-(5-hydroxy-1-(2-hydroxyethyl)-3-methyl-1H-pyrazol-4-yl-methylene)-5-methyl-2,4-dihydropyrazol-3-one (2) |
| 0.6 g | of dipotassium 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazol-3-carboxylic acid |
| 0.5 g | of 2-amino-6-chloro-4-nitrophenol hydrochloride |
| 100.0 g | water, demineralized. |

The foregoing colorant solution was applied to bleached hair. After an exposure time of 20 min at 40° C., the hair was washed with water and dried. The hair color was of a medium brown shade. After the washing test, no color loss was observed visually.

|  | L* | a* | b* | $\Delta E_{1/2}$ | Color loss, % |
|---|---|---|---|---|---|
| Untreated hair | 84.80 | −0.75 | 11.53 |  |  |
| Colored hair | 25.14 | 2.16 | 11.89 | 59.73 |  |
| 5× washed and dried hair | 24.07 | 3.21 | 10.42 | 2.10 | 4 |

Example 8

Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 1.2 g | of 5-(3-(5-cyano-1-ethyl-4-methyl-2,6-dioxo-1,6-dihydro-2H-pyridin-3-ylidene)propenyl-1-ethyl-6-hydroxy-4-methyl-2-oxo-1,2-dihydropyridine-3-carbonitrile (24a) |
| 0.8 g | of tetrasodium 4-(3-(carboxy-5-oxo-1-(4-sulfophenyl)-1,5-dihydropyrazol-4-ylidene)propenyl)-5-hydroxy-1-(4-sulfophenyl)-1H-pyrazol-3-carboxylate (9a) |
| 0.5 g | of dipotassium 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazole-3-carboxylic acid (15a) |
| 0.7 g | of 5-hydroxy-1-(4-sulfophenyl)-4-[(4-sulfophenyl)azo]pyrazole-3-carboxylic acid trisodium salt (C.I. 19140; Acid Yellow No. 23) |
| 100.0 g | water, demineralized. |

The foregoing colorant solution was applied to bleached hair. After an exposure time of 20 min at 40° C., the hair was washed with water and dried. The hair color was of a greenish-blue shade. After the washing test, hardly any color loss was observed visually.

|  | L* | a* | b* | $\Delta E_{1/2}$ | Color loss, % |
|---|---|---|---|---|---|
| Untreated hair | 84.80 | −0.75 | 11.53 |  |  |
| Colored hair | 21.94 | 5.95 | −11.69 | 67.35 |  |
| 5× washed and dried hair | 24.63 | 4.68 | −11.94 | 2.99 | 4 |

Example 9

Colorant

| | |
|---|---|
| 10.0 g | of ethanol |
| 10.0 g | of sodium lauryl alcohol diethylene glycol ether sulfate (28% aqueous solution) |
| 10.0 g | of ammonia (25% aqueous solution) |
| 0.7 g | of 2-(2-hydroxyethyl)-4-(5-hydroxy-1-(2-hydroxyethyl)-3-methyl-1H-pyrazol-4-ylmethylene)-5-methyl-2,4-dihydropyrazol-3-one (2) |
| 1.0 g | of ammonium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile (24b) |
| 1.1 g | of 2-chloro-6-ethylamino-4-nitrophenol |
| 100.0 g | water, demineralized. |

The foregoing colorant solution was applied to bleached hair. After an exposure time of 20 min at 40° C., the hair was washed with water and dried. The hair color was of a medium brown shade.

Example 10

Colorant (Acidic Cream)

| | |
|---|---|
| 2.0 g | of sodium lauryl sulfate |
| 20.0 g | of cetyl alcohol |
| 5.0 g | of glyceryl stearate SE |
| 2.0 g | of lanolin alcohol |
| 12.5 g | of lauryl ether sulfate (28% aqueous solution) |
| 0.3 g | of ammonium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile (24b) |
| 0.4 g | of 2-chloro-6-ethylamino-4-nitrophenol |
| 0.2 g | of N-(2,3-dihydroxy)-2-nitro-4-(trifluoromethyl)aniline |
| 100.0 g | water, demineralized. |

Before use, the cream was mixed with water in a 1:1 proportion and applied to bleached hair. After an exposure time of 20 min at 40° C., the hair was washed with a shampoo and dried. The hair color was of a medium-blond shade.

Example 11

Colorant (Combination with a Cationic Direct Dye)

| | |
|---|---|
| 10.0 g | of ethanol |
| 10.0 g | of polyethylene lauryl ether (25% aqueous solution) |
| 0.5 g | 2-(2-hydroxyethyl)-4-(5-hydroxy-1-(2-hydroxyethyl)-3-methyl-1H-pyrazol-4-ylmethylene)-5-methyl-2,4-dihydropyrazol-3-one (2) |
| 0.2 g | of di[4-diethylamino)phenyl][4-(ethylamino)naphthyl]carbenium chloride (C.I. 42595; Basic Blue No. 7) |
| 100.0 g | water, demineralized. |

The foregoing colorant solution was applied to bleached hair. After an exposure of 20 min at 40° C., the hair was washed with water and dried. The hair color was of a dark-green shade.

Example 12

Colorant with Carrier

| | |
|---|---|
| 5.0 g | of ethanol |
| 2.0 g | of lactic acid |
| 2.0 g | of sodium cocoamphoacetate (50% aqueous solution) |
| 5.0 g | of carrier according to the following Table 1 |
| 1.2 g | of ammonium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile (24b) |
| 0.4 g | of 4-amino-3-nitrophenol |
| 100.0 g | water, demineralized. |

The foregoing colorant solution was applied to bleached hair. After an exposure of 20 min at 40° C., the hair was washed with water and dried. The colorant without the carrier gave a medium-blue shade, and the colorant with the carrier gave intense blue shades.

TABLE 1

| Carrier | Tinting Result | Comments |
|---|---|---|
| No carrier | red-brown | — |
| Washing 5× and drying | strongly bluish brown shade | yellow component is washed out |
| 2-Hydroxymethylthiophene | saturated red-brown | — |
| Washing 5× and drying | saturated red-brown | no measurable color difference, unsensitive to shampooing |

The L*a*b* color values given in the preceding examples were measured with a Minolta Chromameter II color-measuring instrument.

The L-value indicates the brightness (in other words, the lower the L value, the higher is the color intensity). The a-value is a measure of the red content (namely, the higher the a-value the higher is the red content). The b-value is a measure of the blue content of the color, the blue content being the higher the more negative is the b-value.

The value of ΔE indicates the difference in color between the untreated and the colored hair or between the colored and the washed hair. It is determined as follows:

$$\Delta E = \sqrt{(L_1 - L_0)^2 + (a_1 - a_0)^2 + (b_1 - b_0)^2}$$

where $L_0$, $a_0$ and $b_0$ are the values measured before coloring or before the washing test, and $L_1$, $a_1$ and $b_1$ are the values after coloring or after the washing.

The degree of wash-out was determined according to the following expression:

Decolorization, $\% = [1 - (\Delta E_2 / \Delta E_1)] \times 100$

Here, $\Delta E_1$ refers to the coloring step and $\Delta E_2$ to the washing-out step.

Unless otherwise indicated, all percentages given in the present application are by weight.

What is claimed is:

1. Method for the semi-permanent tinting of hair, comprising applying to the hair a colorant composed of
    (a) at least one monomethine or polymethine dye of tautomeric formula (Ia/Ib) or a physiologically tolerated salt thereof $$Z=L—Z'(Ia) \leftrightarrows Z'=L—Z(Ia)$$

wherein Z=L—Z' and Z'=L—Z are tautomers, Z and Z' each, independently of each other is a substitute five-membered or sex-membered heterocyclic ring and in formula (Ia) Z has a C=O— group and Z' has a C—OH— group in said substituted five-membered or six-membered heterocyclic ring whereas in formula (Ib) Z has a C—OH— group and Z' has a C=O— group in said substituted five-membered or six-membered heterocyclic ring, wherein each of said substituted five-membered or six-membered heterocyclic rings is independently selected from the group consisting of pyrazolones, pyridones, isoxazolones, dioxothiazolines, rhodanines, dioxoimidazolidines, thio barbituric acid and barbituric acid; wherein L represents

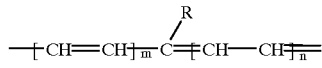

wherein R is hydrogen, a phenyl group, a halogen atom, a methyl group or a carboxamido group, and wherein m and n independently of each other are 0, 1 or 2, with the proviso that n+m does not exceed 2; and
    (b) at least one natural or synthetic non-oxidative dye which is not a monomethine or polymethine dye of tautomeric formula (Ia/Ib);
    allowing an exposure time of 10 to 45 minutes at 20 to 50 C.; rinsing said hair with water; and then drying said hair.

2. The method according to claim 1, further comprising after said rinsing with water and before said drying, washing said hair with a shampoo or rinsing said hair with an aqueous solution of a weak acid.

3. The method according to claim 1, wherein in said formula (Ia) and (Ib), L denotes a monomethine, trimethine or pentamethine unit.

4. The method according to claim 1, wherein said dye of formula (Ia) or (Ib) is selected from dyes of general formulas (II) to (IV)

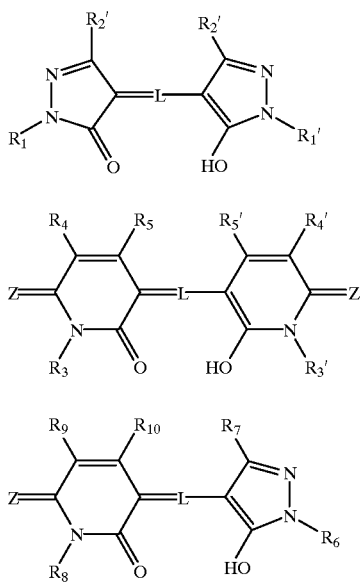

wherein
- R1, R1' denote hydrogen, a straight-chain or branched C1 to C8 alkyl, hydroxyethyl, dihydroxypropyl, methoxyethyl, carboxyethyl or C1 to C4 sulfoalkyl group, a phenyl radical, a phenyl substituted with one or more halogen atoms, a phenyl radical substituted with one or two sulfonic acid groups, a phenyl radical substituted with one or two carboxylic acid groups, a phenyl radical substituted with one or more unbranched or branched C1 to C8 alkyl groups or C1 to C8 alkoxy groups, a benzyl radical, or a benzyl radical substituted with one or more halogen atoms, a benzyl radical substituted with a C1 to C4 alkyl, hydroxyl, methoxy, carboxyl, nitro or amino group or a five-membered or six-membered saturated or unsaturated heterocyclic ring, R1 and R1' being equal or different;
- R2, R2' denote hydrogen, a branched or unbranched C1 to C6 alkyl group, a phenyl radical, an amino group which can also be acylated or sulfonylated, an acetyl or methoxy group or a carboxylic acid group esterified with a straight-chain or branched C1 to C8 alcohol or ethylene glycol monomethyl ether or ethylene glycol monoethyl ether, or a carboxamido, carboxanilido or 2-amino-2-oxyethyl or nitrile group, R2 and R2' being equal or different; and
- R3, R3' and R8 denotes hydrogen, a straight-chain or branched C1 to C11 alkyl group, a straight-chain or branched C1 to C11 monohydroxyalkyl group, a straight-chain or branched C1 to C11 dihydroxyalkyl group, a straight-chain or branched C1 to C11 alkoxyalkyl group, a straight-chain or branched C1 to C11 monoalkylamino group, an amino group having formula $(CH2)_x$—NR11R12 (wherein x stands for an integer from 0 to 3 and R11 and R12 independently of each other denote a C1 to C3 alkyl group), a C2 to C4 sulfoalkyl or carboxyalkyl group, a phenyl group or a phenyl group substituted with one or more halogen atoms, or a phenyl group substituted with one or two sulfonic acid groups, or with one or two carboxyl groups, or with one or more unbranched or branched C1 to C8 alkyl groups or with C1 to C8 alkoxy groups, a benzyl group or a benzyl group substituted with one or more halogen atoms, or with a C1 to C4 alkyl, hydroxyl, methoxy, nitro or amino group, a phenylethyl group, a five-membered or six-membered aromatic or nonaromatic heterocyclic ring which can be linked directly through a methylene group, a pyrolidino, morpholino, piperazino, piperidino or pyridino (C2 or C3) alkyl group or a trialkylammonium group of formula R13—$N(R14)_3^+$ (wherein R13 denotes a C1 to C6 alkylene group and R14 denotes a methyl or ethyl group, the total number of carbon atoms in the group being 5 to 9), R3 and R3' being equal or different, and
- R4, R4' and R9 denotes hydrogen, a nitrile, carboxylate ester, carboxamido, sulfonic acid, sulfomethyl or methanesulfonyl group or a pyridinium or imidazolium radical, R4 and R4' being equal or different, and
- R5, R5' denote hydrogen or a C1 to C4 alkyl or C5–C6 cycloalkyl, phenyl, methoxyphenyl, benzyl, phenylethyl or carboxyl group, R5 and R5' being equal or different, and
- Z denotes oxygen or a radical of formula $C(CN)_2$, C(CN)COOQ or $C(COOQ)_2$ wherein Q denotes a C1 to C8 alkyl group or an ethylene glycol mono-(C3 to C7)-alkyl ether, and
- L denotes a linking group of general formula

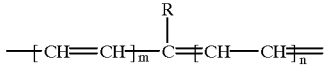

wherein R denotes a hydrogen atom, a phenyl, methyl or carboxamido group or a halogen atom, and the indices m and n equal 0, 1 or 2, the sum of m and n not exceeding 2.

5. The method according to claim 4, wherein the dyes of formulas (II) to (IV) are selected from the group consisting of 4-(5-hydroxy-1,3-dimethyl-1H-pyrazol-4-ylmethylene)-2,5-dimethyl-2,4-dihydropyrazol-3-one; 2-(2-hydroxyethyl)-4-(5-hydroxyethyl-1-(2-hydroxyethyl)-3-methyl-1H-pyrazol-4-ylmethylene)-5-methyl-2,4-dihydropyrazol-3-one; 4-(5-hydroxy-3-methyl-1-(4-sulfophenyl)-1H-pyrazol-4-ylmethylene)-5-methyl-2-(4-sulfophenyl)-2,4-dihydropyrazol-3-one; diammonium 4-(hydroxy-3-methyl-1-(4-sulfophenyl)-1H-pyrazol-4-ylmethylene)-5-methyl-2-(4-sulfophenyl)-2,4-dihyropyrazole-3-one; 4-(3-(5-hydroxy-1,3-dimethyl-1H-pyrazol-4-yl)alkylidene-2,5-dimethyl-2,4-dihydropyrazol-3-one; 5-amino-4-(3-(3-amino-5-hydroxy-1-phenyl-1H-pyrazol-4yl(allylidene)-2-phenyl-2,4-dihydropyrazol-3-one; 2-(2-hydroxyethyl)-4-(3-(5-hydroxy-1(2-hydroxyethyl)-3-methyl-1H-pyrazol-4-yl)allylidene)-5methyl-2,4-dihydropyrazol-3-one; 4-(3-(5-hydroxy-3-methyl-1-(4sulfophenyl)-1H-pyrazol-4yl)allylidene-5methyl-2-(4 -sulfophenyl)-2,4-dihydropyrazol-3one; disodium 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3one; tripotassium 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3-one; 4-(3-(3-carboxy-5-oxo-1-(4-sulfophenyl)-1,5-dihydroxypyrazol-4-ylidene)propenyl)-5-hydroxy-1-(4-sulfophenyl)-1H-pyrazol-3-carboxylic acid; tetrasodium 4-(3-(3-carboxy-5-oxo-1-(4-sulfophenyl)-1,5-dihydropyrazol-4-ylidene)-propenyl)-5-hydroxy-1-(4-sulfophenyl)-1H-pyrazol-3-carboxylic acid; 5-hydroxy-4-

(3-(3-methoxycarbonyl-5-oxo-1-(4-sulfophenyl)-1,5-dihydropyrazol-4-ylidene)-propenyl)-1-(4-sulfophenyl)-1H-pyrazol-3-carboxylic acid methyl ester; 4-(5-(5-hydroxy-1,3-dimethyl-1H-pyrazol-4-yl)penta-2,4-dienylidene)-2,5-dimethyl-2,4-dihydropyrazol-3one; 5-amino-4-(5-(3-amino-5-hydroxy-1-phenyl-1H-pyrazol-4-pyrazol-4-yl)penta-2,4-dienylidene)-2-phenyl-2,4-dihydropyrazol-3-one; 2-(2-hydroxyethyl)-4-(5-(5-hydroxy-1-(2-hydroxyethyl)-3methyl-1H-pyrazol-4-yl)penta-2,4-dienylidene)-5methyl-2,4-dihydropyrazol-3-one; 4-(5-(5-hydroxy-3methyl)-1(4-sulfophenyl-4H-pyrazol-4-yl)penta-2,4-dienylidene)-5-methyl-2-(4-sulfophenyl)-2,4-dihydropyrazol-3-one; dipotassium 4-(5-(5-hydroxy-3-methyl-1-(4-sulfophenyl)-1H-pyrazol-4-yl)penta-2,4-dienylidene)-5-methyl-2-(4-sulfophenyl)-2,4-dihydropyrazol-3-one; 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazol-3-carboxylic acid; dipotassium 4-(5-(3-carboxy-5oxo-1-(4-sulfophenyl)-1,5-dihydropyrazol-4-ylidene)penta-1,3-dienyl)-5-hydroxy-1-(4-sulfophenyl)-1H-pyrazol-3-carboxylic acid; 6-hydroxy-1-(2-hydroxyethyl)-5-(3-(1-(2-hydroxyethyl)-3-methyl-5-oxo-1,5-dihydropyrazol-4-ylidene)propenyl)-4-methyl-2-oxo-1,2-dihydropyridine-3-carbonitrile; 6-hydroxy-5-(3-(1-(2-hydroxyethyl)-3-methyl-5-oxo-1,5-dihydropyrazol-4-ylidene)propenyl)-4-methyl-2-oxo-1-(4-sulfophenyl)-1,2-dihydropyridine-3-carbonitrile; 6-hydroxy-4-methyl-5-(3-(3-methyl-5-oxo-1-(4-sulfophenyl)-1,5-dihydropyrazol-4-ylidene)propenyl)-2-oxo-1-(4sulfophenyl)-1,2-dihydropyridine-3-carbonitrile; 6-hydroxy-4-methyl-5-(3-(3-methyl-5-oxo-1-phenyl-1,5-dihydropyrazol-4-ylidene)propenyl)-2-oxo-1-(3-sulfophenyl)-1,2-dihydropyridine-3-carbonitrile; 4-(3-(5-cyano-2-hydroxy-4-methyl-6-oxo-1-phenyl-1,6-dihydropyridin-3-yl)allylidene)-5-oxo-1-(4-sulfophenyl)-4,5-dihydro-1H-pyrazole-3-carboxylic acid; 6-hydroxy-5-(3-(1-(2-hydroxyethyl)-3-methyl-5-oxo-1,5-dihydropyrazol-4-ylidene)propenyl)-4-methyl-2-oxo-1-phenyl-1,2-dihydropyridine-3-carbonitrile; 5-(3-(4-carboxy-2,6-dioxo-1,6-dihydro-2H-pyridin-3-ylidene)propenyl)-6-hydroxy-2oxo-1,2-dihydropyridine-4-carboxylic acid; 2-(3-cyano-5-(3-(5-cyano-6-dicyanomethylene-4-methyl-2-oxo-1,6-dihydro-2H-pyridin-3-ylidene)propenyl)-6-hydroxy-4-methyl-1H-pyridin-2-ylidene)malononitrile; 5-(3-(5-cyano-1-ethyl-4-methyl-2,6-dioxo-1,6-dihydro-2H-pyridin-3-ylidene)propenyl)1-ethyl-6-hydroxy-4-methyl-2-oxo-1,2dihydropyridine-3-carbonitrile; triethylammonium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; 5-(3-(5-cyano-1-(2-hydroxyethyl)-4-methyl-2,6-dioxo-1,6-dihydro-2H-pyridin-3-ylidene)propenyl)-6-hydroxy-1-(2-hydroxyethyl)-4-methyl-2-oxo-1,2-dihydropyridine-3-carbonitrile; 5-(3-(5-cyano-1-ethyl-4-(4-methoxyphenyl)-2,6-dioxo-1,6-dihydro-2H-pyridin-3-ylidene)propenyl)-1-ethyl-6-hydroxy-4-(4-methoxyphenyl)-2-oxo-1,2-dihydropyridine-3-carbonitrile; 1-butyl-5-(3-(1-butyl-5-cyano-4-methyl-2,6-dioxo-1,6-dihydro-2H-pyridin-3-ylidene)propenyl)-6-hydroxy-4-methyl-2-oxo-1,2-dihydropyridine-3-carbonitrile; 5-(3-(5-cyano-1-(3-methoxypropyl)-4-methyl-2,6-dioxo-1,6-dihydro-2H-pyridin-3-ylidene)propenyl)-1-ethyl-6-hydroxy-1-(3-methoxypropyl)-4-methyl-2-oxo-1,2-dihydropyridine-3-carbonitrile; 5-(3-(5-cyano-1-cyclohexyl-4-methyl-2,6-dioxo-1,6dihydro-2H-pyridin-3-ylidene)-propenyl)-1-ethyl-6-hydroxy-4-methyl-2-oxo-1,2-dihydropyridine-3-carbonitrile; 5-(3-(5-cyano-4-methyl-1-(2-morpholin-4-ylethyl)-2,6-dioxo-1,6-dihydro-2H-pyridin-3-ylidene)propenyl)-6-hydroxy-4-methyl-1-(2-morpholin-4-ylethyl)-2-oxo-1,2-dihydropyridine-3-carbonitrile; 5-(3-(5-cyano-4-methyl-2,6-dioxo-1-(4-sulfophenyl-1,6-dihydro-2H-pyridin-3-ylidene)propenyl)-6-hydroxy-4-methyl-2-oxo-1-(4-sulfophenyl)-1,2-dihydropyridine-3-carbonitrile; 5-(3-(5-cyano-4-methyl-2,6-dioxo-1-(3-sulfophenyl)-1,6-dihydro-2H-pyridin-3-ylidene)propenyl)-6-hydroxy-4-methyl-2-oxo-1-(3-sulfophenyl)-1,2-dihydropyridine-3-carbonitrile; 5-(3-(5-cyano-1-dimethylamino-4-methyl-2,6-dioxo-1,6dihydro-2H-pyridin-3-ylidene)propenyl)-1-dimethylamino-6-hydroxy-4-methyl-2-oxo-1,2-dihydropyridine-3-carbonitrile; 5-(3-(5-carbamoyl-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carboxamide; 1-ethyl-3-(3-(1-ethyl-2-hydroxy-5-methanesulfonyl-4-methyl-6-oxo-1,6-dihydropyridin-3-yl)allylidene)-5-methanesulfonyl-4-methyl-3H-pyridine-2,6-dione; 5-(5-(5-cyano-1-ethyl-4-methyl-2,6-dioxo-1,6-dihydro-2H-pyridin-3-ylidene)penta-1,3-dienyl)-1-ethyl-6-hydroxy-4-methyl-2-oxo-1,2-dihydropyridine-3-carbonitrile and ammonium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile.

6. The method according to claim 1, wherein said physiologically tolerated salt is selected from the group consisting of the ammonium, sodium, potassium, triethylammonium, N-methylmorpholinium, monoethanolammonium, diethanolammonium and triethanolammonium salts.

7. The method according to claim 1, wherein said colorant has a pH value of from 2 to 11.

8. The method according to claim 1, wherein said colorant contains from 0.01 to 5% by weight of said dye of formula (Ia/Ib).

9. The method according to claim 1, wherein said colorant contains from 0.01 to 15% by weight of said non-oxidative dye.

10. The method according to claim 1, wherein said non-oxidative dye is selected from the group consisting of natural dyes, nitro dyes, azo dyes, quinone dyes, triphenylmethane dyes and basic or acid dyes.

* * * * *